United States Patent
Dykas et al.

(10) Patent No.: US 11,795,430 B2
(45) Date of Patent: Oct. 24, 2023

(54) THIN FILM DEPOSITED INORGANIC METAL OXIDE AS A SELECTIVE SUBSTRATE FOR MAMMALIAN CELL CULTURE AND AS AN IMPLANT COATING

(71) Applicants: National University of Singapore, Singapore (SG); Agency for Science, Technology and Research, Singapore (SG)

(72) Inventors: Michal Marcin Dykas, Singapore (SG); Kingshuk Poddar, Singapore (SG); Xuefeng Hu, Singapore (SG); Ee Jen Wilson Wang, Singapore (SG); Thirumalai Venky Venkatesan, Singapore (SG); Abhijeet Patra, Singapore (SG); Viknish Krishnan Kutty, Singapore (SG); Paul Lorenz Bigliardi, Singapore (SG); Mei Bigliardi, Singapore (SG)

(73) Assignees: National University of Singapore, Singapore (SG); Agency for Science, Technology, and Research, Singapore (SG)

( * ) Notice: Subject to any disclaimer, the term of this patent is extended or adjusted under 35 U.S.C. 154(b) by 661 days.

(21) Appl. No.: 16/348,838

(22) PCT Filed: Nov. 10, 2017

(86) PCT No.: PCT/SG2017/050567
§ 371 (c)(1),
(2) Date: May 9, 2019

(87) PCT Pub. No.: WO2018/088966
PCT Pub. Date: May 17, 2018

(65) Prior Publication Data
US 2019/0345438 A1 Nov. 14, 2019

Related U.S. Application Data

(60) Provisional application No. 62/420,812, filed on Nov. 11, 2016.

(51) Int. Cl.
| | |
|---|---|
| *A61L 27/10* | (2006.01) |
| *C12N 5/00* | (2006.01) |
| *C12N 5/0793* | (2010.01) |
| *C12N 5/0797* | (2010.01) |
| *C12N 5/071* | (2010.01) |
| *C12N 5/077* | (2010.01) |
| *C23C 14/08* | (2006.01) |

(52) U.S. Cl.
CPC ............ *C12N 5/0018* (2013.01); *A61L 27/10* (2013.01); *C12N 5/0068* (2013.01); *C12N 5/0619* (2013.01); *C12N 5/0623* (2013.01); *C12N 5/0629* (2013.01); *C12N 5/0653* (2013.01); *C12N 5/0654* (2013.01); *C12N 5/0656* (2013.01); *C23C 14/083* (2013.01); *C23C 14/086* (2013.01); *C23C 14/087* (2013.01); *C12N 2533/12* (2013.01); *C12N 2533/52* (2013.01); *C12N 2535/10* (2013.01)

(58) Field of Classification Search
None
See application file for complete search history.

(56) References Cited

U.S. PATENT DOCUMENTS

| | | | | |
|---|---|---|---|---|
| 5,037,438 A | * | 8/1991 | Davidson | A61L 27/306 623/22.15 |
| 5,632,779 A | * | 5/1997 | Davidson | A61F 2/06 623/1.51 |
| 6,869,701 B1 | * | 3/2005 | Aita | A61L 27/50 623/1.46 |
| 2003/0003329 A1 | * | 1/2003 | Wang | C04B 41/009 427/446 |
| 2005/0039672 A1 | | 2/2005 | Selvamanickam et al. | |
| 2006/0251875 A1 | | 11/2006 | Carlisle et al. | |
| 2008/0102321 A1 | | 5/2008 | Buehlmann et al. | |
| 2009/0317767 A1 | * | 12/2009 | Burger | C04B 35/62815 433/201.1 |
| 2010/0086896 A1 | | 4/2010 | Gieselmann et al. | |

FOREIGN PATENT DOCUMENTS

| | | |
|---|---|---|
| CN | 1742112 A | 3/2006 |
| JP | H1176836 A | 3/1999 |

OTHER PUBLICATIONS

Almaguer-Flores et al., Materials Science and Engineering C 57 (2015) 88-99 (Year: 2015).*
Memarzadeh et al., Journal of Biomedical Materials Research A, Mar. 2015, vol. 103A, Issue 3, pp. 981-989 (Year: 2015).*
Visai et al., Int J Artif Organs 2011; 34 (9): 929-946 (Year: 2011).*
Heiroth et al., Acta Materialia 59 (2011) 2330-2340 (Year: 2011).*
Kirmanidou et al., BioMed Research International, vol. 2016, Article ID 2908570, 21 pages (Year: 2016).*

(Continued)

*Primary Examiner* — Evelyn Y Pyla
(74) *Attorney, Agent, or Firm* — Fletcher Yoder P.C.

(57) ABSTRACT

Disclosed herein is a material that may be useful as a coating for optical slides and medical implants. The material may aid or restrict grown of cells on a coating of the composite material. As such, there is provided a composite material having a substrate on the surface of which a coating layer of an amorphous metal oxide is formed. The metal oxide may be one or more of $Ag_2O$, $ZnO$, $ZrO_2$, $TiO_2$, $CuO$, and $Y_2O_3$ and the coating layer may be from 5 to 100 nm thick and have a root mean square roughness of the coating surface is from 0.1 to 0.7 nm.

13 Claims, 11 Drawing Sheets

(56) References Cited

OTHER PUBLICATIONS

Liu et al Adv. Funct. Mater. 2015, 25, 7180-7188 (Year: 2015).*
Chinese Search Report Application No. 201780069905.6, dated Nov. 19, 2020 (3 pages).
Chinese Office Action Application No. 201780069905.6, dated Dec. 3, 2020 (4 pages).
European Search Report Application No. 17869935.1, dated Aug. 18, 2020 (17 Pages).
European Search Report Application No. 17869935.1, dated May 14, 2020 (20 Pages).
Written Opinion from PCT Application No. PCT/SG2017/050567, dated Jan. 29, 2018 (6 pages).
S. K. Desai, et al.; "The horizontally-acquired response regulator SsrB drives a *Salmonella* lifestyle switch by relieving biofilm silencing;" Elife; Feb. 2, 2016; 5, e10747 (23 pages).
H. M. Christens, et al.; "Continuous compositional-spread technique based on pulsed-laser deposition and applied to the growth of epitaxial films;" Review of Scientific Instruments; May 23, 2001; 72, 2673-2678 (7 pages).
R. Donato, et al.; "Differential development of neuronal physiological responsiveness in two human neural stem cell lines;" BMC Neuroscience; May 25, 2007; 8, 36 (11 pages).
Silva-Bermudez, P. et al., Enhancing the osteoblastic differentiation through nanoscale surface modifications. Journal of Biomedical Materials Research Part A, Oct. 31, 2016, vol. 105, No. 2, pp. 498-509.
Almaguer-Flores, A. et al., Bacterial adhesion on amorphous and Almaguer-Flores, A. et al., Bacterial adhesion on amorphous and 2015, vol. 57, pp. 88-99.
Kim, Y.-H. et al., A Pixel-Isolated Flexible Liquid Crystal Display with a Homogeneous Alignment on an Amorphous Zr02 Thin Film. Electrochemical and Solid-State Letters, Sep. 27, 2010, vol. 13, No. 12, pp. J143-J145.
Shailin, Z. et al., Biological behavior of osteoblast-like cells on titania and zirconia films deposited by cathodic arc deposition. Biointerphases, Oct. 2, 2012, vol. 7, pp. 60: 1-1 O.
PCT International Search Report for PCT Application No. PCT/SG2017/050567; 5 Pages.

* cited by examiner a)

b)

c)

a)

b)

c)

a)

b)

THIN FILM DEPOSITED INORGANIC METAL OXIDE AS A SELECTIVE SUBSTRATE FOR MAMMALIAN CELL CULTURE AND AS AN IMPLANT COATING

FIELD OF INVENTION

The current invention relates to a thin film of a material that may be used to aid or impede the growth of cells, and may be used on any surface that requires such a property, such as imaging slides and/or implant materials.

BACKGROUND

For research purposes, it is important to be able to image cells in various stages of the cell cycle. In order to achieve this, one needs to have a cell culture substrate material that can allow for the growth of the cells to be imaged. This is not always an easy task, as different mammalian tissue types may refuse to grow on standard surfaces, such as that provided by a glass slide. As such, there is a need for new materials that may help facilitate cell imaging in various growth phases.

Medical implants are widely used to compensate for bodily defects, whether from a congenital condition or through the acquisition of a defect by disease or trauma. Examples of such implants include sensory and neurological implants, cardiovascular implants, orthopedic implants, contraceptive implants, cosmetic implants and the like. A feature common to all of these implants is that they are in intimate contact with one or more tissues of the body following implantation. This tissue may be, for example bone tissue and/or one or more soft tissues, such as muscular tissue, connective tissues, epithelial tissue and mucosal tissue. While it is always desirable for the implant to be compatible with the tissue(s) it is in contact with, whether the implant acts as a scaffold for the growth of new tissues or acts to prevent growth depends on whether the implant is intended to be permanent or temporary and on the type of medical treatment being undertaken. While various coatings have been developed for implants, these may not be suited for use across a wide variety of tissue types and so there remains a need for new coatings for implants that may encourage or discourage tissue bonding and integration as desired.

SUMMARY OF INVENTION

The invention is summarised in the following numbered aspects and embodiments.

1. A composite material comprising:
   a substrate having a surface; and
   an amorphous metal oxide coating on the surface of said substrate, where the coating has a surface, wherein:
   the metal oxide is selected from one or more of the group consisting of $Ag_2O$, $ZnO$, $ZrO_2$, $TiO_2$, $CuO$, and $Y_2O_3$; and
   the metal oxide coating on the substrate surface is from 5 nm to 100 nm thick (e.g. from 5 nm to 50 nm, or from 5 to 25 nm thick)

2. The composite material according to Clause 1, wherein the metal oxide is selected from two or more of $Ag_2O$, $ZnO$, $ZrO_2$, $TiO_2$, $CuO$, and $Y_2O_3$.

3. The composite material according to Clause 2, wherein the metal oxide is selected from two or three of $Ag_2O$, $ZnO$, $ZrO_2$, $TiO_2$, $CuO$, and $Y_2O_3$.

4. The composite material according to any one of the preceding clauses, wherein the metal oxide is selected from $ZrO_2$ and/or $Y_2O_3$.

5. The composite material according to any one of the preceding clauses, wherein when there are two or more metal oxides, the wt % content of each metal oxide varies throughout the coating, such that at any given location one of the metal oxides is present in an amount of from 0 wt % to 100 wt %.

6. The composite material according to Clause 5, wherein the wt % content of each metal oxide varies throughout the coating, such that at any given location one of the metal oxides is present in an amount of from 5 wt % to 95 wt %.

7. The composite material according to any one of Clauses 1 to 4, wherein when there are two or more metal oxides, the wt % content of each metal oxide is constant throughout the coating, such that each metal oxide is present in an amount of from 0.1 wt % to 99.5 wt %.

8. The composite material according to Clause 7, wherein each metal oxide is present in an amount of from 1 wt % to 99 wt % throughout the coating, such as from 5 wt % to 90 wt %.

9. The composite material according to Clause 8, wherein each metal oxide is present in an amount of from 15 wt % to 85 wt % throughout the coating, such as from 40 wt % to 60 wt %.

10. The composite material according to Clause 7, wherein there the two metal oxides are $ZrO_2$ and $Y_2O_3$, and $ZrO_2$ is present in an amount of from 1 wt % to 99 wt % throughout the coating, with the balance being $Y_2O_3$.

11. The composite material according to Clause 10, wherein $ZrO_2$ is present in an amount of from 5 wt % to 90 wt % throughout the coating, with the balance being $Y_2O_3$.

12. The composite material according to Clause 11, wherein $ZrO_2$ is present in an amount of from 10 wt % to 90 wt % throughout the coating, with the balance being $Y_2O_3$.

13. The composite material according to Clause 12, wherein $ZrO_2$ is present in an amount of from 15 wt % to 85 wt % throughout the coating, with the balance being $Y_2O_3$.

14. The composite material according to Clause 13, wherein $ZrO_2$ is present in an amount of from 20 wt % to 80 wt % throughout the coating, with the balance being $Y_2O_3$.

15. The composite material according to Clause 14, wherein $ZrO_2$ is present in an amount of from 40 wt % to 75 wt % throughout the coating, with the balance being $Y_2O_3$.

16. The composite material according to Clause 15, wherein $ZrO_2$ is present in an amount of from 50 wt % throughout the coating, with the balance being $Y_2O_3$.

17. The composite material according to any one of the preceding clauses, wherein:
   (a) the substrate is selected from the group consisting of titanium and silicon oxide (e.g. quartz); and/or
   (b) the metal oxide coating has a surface roughness, which surface roughness may be a root mean square roughness of from 0.1 to 0.7 nm.

18. The composite material according to any one of the preceding clauses, wherein the substrate is in the form of a transparent slide suitable for microscopy or in the form of a medical implant.

19. The composite material according to Clause 18, wherein the substrate is a temporary medical implant (e.g. a temporary catheter, a temporary bone screw, a contact lens) where the coating comprises from 65 to 100 wt % of $Y_2O_3$ (e.g. from 80 to 100 wt % of $Y_2O_3$).

20. The composite material according to Clause 18, wherein the substrate is a permanent medical implant where the coating comprises from 50 to 100 wt % of $ZrO_2$ (e.g. from 80 to 100 wt % of $ZrO_2$).

21. The composite material according to Clause 18, wherein the substrate is a intraocular lens where the coating comprises from 65 to 100 wt % of $Y_2O_3$ (e.g. from 80 to 100 wt % of $Y_2O_3$).

22. A method of manufacturing a composite material, the process comprising the steps of:
   (a) providing a substrate having a surface and depositing a metal oxide onto said surface using Pulsed Laser Deposition; and
   (b) sintering the resulting material at a temperature of up to 250° C. to form an amorphous metal oxide coating on the surface of the substrate wherein:
   the metal oxide is selected from one or more of the group consisting of $Ag_2O$, ZnO, $ZrO_2$, $TiO_2$, CuO, and $Y_2O_3$; and
   the metal oxide coating on the substrate surface is from 5 nm to 100 nm thick (e.g. from 5 nm to 50 nm thick, such as from 5 nm to 25 nm thick).

23. The method according to Clause 22, wherein the metal oxide is selected from two or more of $Ag_2O$, ZnO, $ZrO_2$, $TiO_2$, CuO, and $Y_2O_3$, such as from two or three of $Ag_2O$, ZnO, $ZrO_2$, $TiO_2$, CuO, and $Y_2O_3$, and where step (a) uses Pulsed Laser Deposition or Pulsed Laser Deposition Continuous Composition Spread Technique.

24. The method according to Clause 22 or Clause 23, wherein the metal oxide is selected from $ZrO_2$ and/or $Y_2O_3$, and where step (a) uses Pulsed Laser Deposition or Pulsed Laser Deposition Continuous Composition Spread Technique.

25. The method according to any one of the preceding clauses, wherein when there are two or more metal oxides, the wt % content of each metal oxide varies throughout the coating, such that at any given location one of the metal oxides is present in an amount of from 0 wt % to 100 wt %.

26. The method according to Clause 25, wherein the wt % content of each metal oxide varies throughout the coating, such that at any given location one of the metal oxides is present in an amount of from 5 wt % to 95 wt %.

27. The method according to any one of Clauses 22 to 25, wherein when there are two metal oxides, the metal oxides are $ZrO_2$ and $Y_2O_3$:
   (a) $ZrO_2$ is present in an amount of from 1 wt % to 99 wt % throughout the coating, with the balance being $Y_2O_3$;
   (b) $ZrO_2$ is present in an amount of from 5 wt % to 90 wt % throughout the coating, with the balance being $Y_2O_3$;
   (c) $ZrO_2$ is present in an amount of from 10 wt % to 90 wt % throughout the coating, with the balance being $Y_2O_3$;
   (d) $ZrO_2$ is present in an amount of from 15 wt % to 85 wt % throughout the coating, with the balance being $Y_2O_3$;
   (e) $ZrO_2$ is present in an amount of from 20 wt % to 80 wt % throughout the coating, with the balance being $Y_2O_3$;
   (f) $ZrO_2$ is present in an amount of from 40 wt % to 75 wt % throughout the coating, with the balance being $Y_2O_3$; or
   (g) $ZrO_2$ is present in an amount of from 50 wt % throughout the coating, with the balance being $Y_2O_3$.

28. The method according to any one of Clauses 22 to 25, wherein:
   (a) the substrate is selected from the group consisting of titanium and silicon oxide (e.g. quartz); and/or
   (b) the metal oxide coating has a surface roughness, which surface roughness may be a root mean square roughness of from 0.1 to 0.7 nm.

29. The method according to any one of Clauses 22 to 28, wherein the sintering step is conducted at a temperature of up to 200° C.

30. A method of growing cells on a composite material according to any one of Clauses 1 to 21, said method comprising the steps of:
   (a) providing a composite material according to any one of Clauses 1 to 21 and a first cell population;
   (b) applying the first cell population to the composite material; and
   (c) culturing the first cell population on the composite material to form a second cell population.

31. The method according to Clause 30, wherein the cell population cells are selected from one or more of the group consisting of keratinocytes, fibroblasts, neural crest cells, neural stem cells, adipocytes, osteoblasts and bacterial cells (e.g. *salmonella* and *E. coli* cells).

32. The method according to Clause 30 or Clause 31, wherein the method does not involve coating the composite material with extracellular coating and/or laminin coating.

33. The method according to any one of Clauses 30 to 32, wherein the method further comprises imaging the cells following step (b) of Clause 30.

DESCRIPTION

Figure 1:
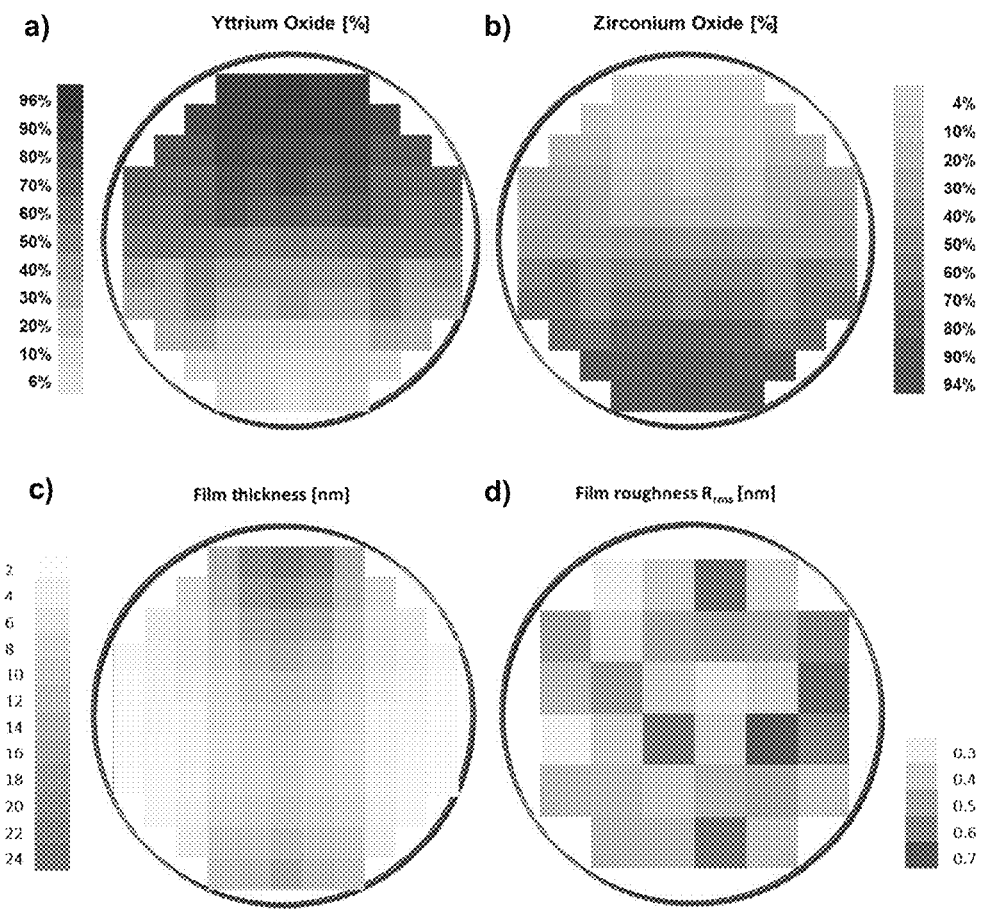
FIG. 1 Chemical characterisation of the material on the substrates. (a) Concentration of yttrium oxide and (b) zirconium oxide across the substrate. The amount of one of the oxides decreased from one side to the other side, resulting in the variation of elemental ratios. (c) Thickness and (d) roughness of the material library, calculated from the AFM images of the surface on the coated substrate.

It has been surprisingly found that coating a substrate material with a thin coating of certain metal oxides provides the resulting surface with cell adhesion and cell growing properties or the opposite—that is no cell adhesion takes place. Yet more surprisingly, for certain cell types a blend of certain of these metal oxides may provide greater adhesion than would otherwise have been expected. Thus, there is provided a composite material comprising:

a substrate having a surface; and an amorphous metal oxide coating on the surface of said substrate, where the coating has a surface, wherein:

the metal oxide is selected from one or more of the group consisting of $Ag_2O$, ZnO, $ZrO_2$, $TiO_2$, CuO, and $Y_2O_3$; and the metal oxide coating on the substrate surface is from 5 nm to 100 nm thick.

Without wishing to be bound by theory, it is believed that the use of a thin amorphous metal oxide coating is responsible for the properties obtained herein. It is noted that the thinness of the metal oxide coating may result in a transparent layer of material that may therefore be useful in the manufacture of slides for microscopy and the like or for use in eye implants (both temporary and permanent). In addition, without wishing to be bound by theory, it is noted that the thinness of the metal oxide layer may reduce the brittleness normally associated with such metal oxide coatings, making them useable in medical implants as discussed herein.

The thickness of the metal oxide layer may be from 5 nm to 100 nm. In alternative embodiments, the thickness of the metal oxide layer may be from 5 nm to 50 nm, such as from 5 nm to 25 nm. It will be appreciated that a relatively thin metal oxide layer may be more transparent and/or less brittle than a relatively thick metal oxide layer (when compared to each other). In certain embodiments, the metal oxide coating may also be smooth. The surface roughness may be measured as a root mean square roughness that may be from 0.1 to 0.7 nm In embodiments herein, the word "comprising" may be interpreted as requiring the features mentioned, but not limiting the presence of other features. Alternatively, the word "comprising" may also relate to the situation where only the components/features listed are intended to be present (e.g. the word "comprising" may be replaced by the phrases "consists of" or "consists essentially of"). It is explicitly contemplated that both the broader and narrower interpretations can be applied to all aspects and embodiments of the present invention. In other words, the word "comprising" and synonyms thereof may be replaced by the phrase "consisting of" or the phrase "consists essentially of" or synonyms thereof and vice versa.

In certain embodiments that may be mentioned herein, the composite material may only contain one metal oxide selected $Ag_2O$, ZnO, $ZrO_2$, $TiO_2$, CuO, and $Y_2O_3$. For example, in embodiments where it is desired that a medical implant does not encourage growth of cells on the surface, the only metal oxide used may be $Y_2O_3$ which is demonstrated herein to prevent cell adhesion and/or cell growth on the coated substrate. In contrast, where cell growth and adhesion is to be encouraged in a medical implant (or on a slide for imaging), the metal oxide may be $Y_2O_3$ or, more particularly, $ZrO_2$ to adhere and grow a range of different cell types when used alone.

Alternatively, the metal oxide may be selected from two or more of $Ag_2O$, $ZnO$, $ZrO_2$, $TiO_2$, $CuO$, and $Y_2O_3$. For example, the metal oxide may be selected from two or three of $Ag_2O$, $ZnO$, $ZrO_2$, $TiO_2$, $CuO$, and $Y_2O_3$. In particular embodiments described herein, the metal oxide may be selected from $ZrO_2$ and $Y_2O_3$. As will be described in detail hereinbelow, the combination of two or more metal oxides in the coatings described herein result in a blended coating material that may have superior properties compared to either material alone. For example, the use of both $ZrO_2$ and $Y_2O_3$ in a coating material (e.g. at a weight ratio of 50:50) may provide increased cell adhesion and growth for certain cell types (e.g. mature adipocytes) than either material alone.

As will be appreciated, when there are two or more metal oxides, the weight percentage of each metal oxide may be a fixed percentage across the entirety of the coating layer or it may vary. This may depend on the application that the coating layer is be used for. For example, in a medical implant, it may be desired to enable growth and adhesion of cell tissue on the coating surface (and thereby on the implant) in only certain areas, while preventing or minimising growth and adhesion on other areas. This may be achieved by selecting an appropriate coating material for the various areas of the implant. For example, in an area that is intended for cell adhesion, the coating may only comprise $Y_2O_3$ or, more particularly, $ZrO_2$ (i.e. 100 wt % of $ZrO_2$) or a blend high in $ZrO_2$ (e.g. 80 wt % $ZrO_2$ and 20 wt % $Y_2O_3$) or (depending on the cells to be adhered) a blend of 50:50 wt % $ZrO_2$ and $Y_2O_3$. In contrast, in areas that are to be free of cell adhesion, the intended cell-free areas may be coated only with $Y_2O_3$ or a $Y_2O_3$-rich blend (e.g. 80 wt % $Y_2O_3$ and 20 wt % $ZrO_2$). While the above is described with reference to a medical implant, it will be appreciated that it may also relate to optical slides, a culturing surface or in a reactor (e.g. where a patterned surface of cells is desired). The desired areas may be discrete, such that a coating area having 80 wt % $Y_2O_3$ and 20 wt % $ZrO_2$ may immediately abut with a different area having 80 wt % $ZrO_2$ and 20 wt % $Y_2O_3$ (this may be achieved by pulsed laser deposition). Alternatively, in embodiments where a gradient between the two extremes is desired, the blended layers may be provided by the Pulsed Laser Deposition Continuous Composition Spread Technique.

As disclosed herein in the examples section, mammalian cells, such as primary human adult fibroblasts, human embryonic stem cells derived fibroblasts, primary human keratinocytes, human osteocytes, human midbrain derived neural stem cells, dog kidney epithelial cells, and rat schwannomas had improved adherence, migration, proliferation and differentiation on inorganic thin film deposited glass substrates that contain more zirconium oxide as opposed to wafers containing more yttrium oxide, which were avoided (e.g. 60 wt % $ZrO_2$, such as 80 wt % $ZrO_2$ as discussed herein, with the balance being other metal oxides, such as yttrium oxide). Other cell types, however, such as mouse adipocytes and human embryonic stem cell-derived neural crest cells preferred a region with an equal mix of oxides (i.e. approximately 50:50 wt % $ZrO_2$ and $Y_2O_3$), while one line of human melanoma cells preferred the yttrium oxide region (e.g. 60 wt % $Y_2O_3$, such as 80 wt % $Y_2O_3$ as discussed herein, with the balance being other metal oxides, such as $ZrO_2$). This proves that various metal oxides and its combinations have different effects on adhesion of mammalian and non-mammalian cells and this can be used as coating in lab technology, diagnostic or devices for treatment for specific and tailored applications Given the above, it will be appreciated that when there are two or more metal oxides, the wt % content of each metal oxide may vary throughout the coating, such that at any given location one of the metal oxides is present in an amount of from 0 wt % to 100 wt %. In other words, each location may represent a blend of two or more metal oxides or only one metal oxide is present at that location. For example, in certain embodiments, it may be convenient to ensure that there is at least a certain amount of the other metal oxide present when there are two or more metal oxides present. As such, the wt % content of each metal oxide varies throughout the coating, such that at any given location one of the metal oxides is present in an amount of from 5 wt % to 95 wt %.

In alternative medical implants and/or slides, it may be desirable to use a metal oxide coating that is constant throughout. In such cases, where there are two metal oxides, the wt % content of each metal oxide is constant throughout the coating, such that each metal oxide may be present in an amount of from 0.1 wt % to 99.5 wt %. For example, each metal oxide is present in an amount of from 1 wt % to 99 wt % throughout the coating, such as from 5 wt % to 90 wt %, from 15 wt % to 85 wt %, such as from 40 wt % to 60 wt %, such as 50 wt %.

As mentioned hereinbefore, when there are two metal oxides present in a coating layer, the two metal oxides may be $ZrO_2$ and $Y_2O_3$. In such case, $ZrO_2$ may be present in an amount of from 1 wt % to 99 wt % throughout the coating, with the balance being $Y_2O_3$. For example, $ZrO_2$ is present in an amount of from 5 wt % to 90 wt %, such as from 10 wt % to 90 wt %, such as from 15 wt % to 85 wt %, such as from 20 wt % to 80 wt %, such as from 40 wt % to 75 wt % (e.g. 50 wt %) throughout the coating, with the balance being $Y_2O_3$.

One of the surprising findings of the current invention is that a coating layer comprising a blend of $ZrO_2$ and $Y_2O_3$ (e.g. 50:50 wt %) results in the improved adhesion of peripheral neural cells, which enables the facilitation of long term co-culture experiments, which were not possible on traditional cell culture glass coverslips. This allowed for the enhanced performance of electron microscopy (compared to plastic coverslips) and other high resolution light microscopy techniques on these peripheral neurons, which would otherwise not be possible. Moreover, on normal glass slides the cells detached over long periods of culture. The experiments detailed hereinbelow show that the preference of cells to particular regions is due to their preferred adhesion to those regions.

The above materials and methods enable the manipulation of cellular behaviour using surface chemistry to render cells adherent (or non-adherent) in culture or in vivo across species and different cellular types. Particular metal oxide combinations that allow cells of different types to adhere, to not adhere and to differentiate are disclosed herein in the examples. Though the data presented herein only considers the combination of two metal oxides at different weight percentage ratios in-depth, it nevertheless shows how different cell types have distinct preferences to specific oxide combinations; some oxide combinations may be used to promote cell adhesion while others may be used to deter cell adhesion. Increasing the metal oxide types in the combinatorial library to contain a more diverse mix, would logically yield more varied influences to cellular processes that can be used, which has been explored somewhat herein.

Based on the disclosures herein, it is known that cells have different adhesive characteristics to different ratios of oxide combinations. For mammalian cells, though both $Y_2O_3$ and $ZrO_2$ are similar (the metals only differing by one atomic number) and have oxide thickness, roughness, wettability, surface energy and other mechanical properties to be of negligible differences across the substrate, they still prompt different effects on different cellular processes. For bacterial cells, the distribution of the biofilm was not directly correlated with any of the individual components but is the result of the combination of the oxides. Some combinations of oxides provide unique properties which disable biofilm formation, such as Zinc, which has known antibacterial properties. However, as Zinc by itself is toxic, this novel method may potentially be able to reduce its general toxicity to mammalian cells, while preventing biofilm formation.

Any suitable substrate material may be used to support the amorphous metal oxide coatings described herein. Suitable substrate materials include, but are not limited to titanium and silicon oxide (e.g. quartz). The substrate material may be in any suitable form. For example, the substrate may be in the form of a transparent slide suitable for microscopy, the lining of a reaction vessel or in the form of a medical implant. Any suitable medical implant with a suitable substrate may be coated in the manner described herein (and as desired). Such medical implants may be temporary medical implants or they may be permanent medical implants.

Temporary medical implants may include, but are not limited to, a temporary catheter, a temporary bone screw, and a contact lens. These implants are temporary because they are applied to (or inserted into) the body for a certain period of time before being removed and/or replaced. As such, it may be advantageous to coat these implants with a metal oxide material that discourages or inhibits cell adhesion and growth on the implant, as this may make it more difficult to remove the implant at the end of its period of use. An example of a suitable metal oxide coating as described herein would be an implant where the coating layer comprises from 65 to 100 wt % of $Y_2O_3$ (e.g. from 80 to 100 wt % of $Y_2O_3$). A similar coating layer may be useful where the implant is intended to remain in the body permanent, but in a location where cell adhesion and growth would be detrimental to the functioning of the implant. For example, an intraocular lens should remain free of lens cells, otherwise its function may be compromised, which intraocular lens may have a metal oxide coating layer that comprises from 65 to 100 wt % of $Y_2O_3$ (e.g. from 80 to 100 wt % of $Y_2O_3$).

In other permanent implants, it may be desired to have cells become adhered to and grow on the implant, which has been described in some detail hereinbefore. As noted hereinabove, such implants may have a coating layer that comprises from 50 to 100 wt % of $ZrO_2$ (e.g. from 80 to 100 wt % of $ZrO_2$).

When an optical slide and/or culturing vessel are intended to provide the maximum amount of the desired cells, the entire working surface of said slide/vessel may be coated with the desired metal oxide(s) so as to ensure that the maximum yield of the desired cells is achieved.

As will be appreciated, any product mentioned herein is also specifically intended to form part of the currently claimed invention. As such, there are also provided, medical implants, optical slides, reaction vessels, and culturing vessels that comprise the metal oxide coating layer discussed herein. Said products may use any of the coating layers discussed herein.

The coating surfaces described above may be manufactured using a Pulsed Laser Deposition or variants thereof, which allows one or more materials to be deposited onto a substrate. Said process may comprise the steps of:
 (a) providing a substrate having a surface and depositing a metal oxide onto said surface using Pulsed Laser Deposition; and
 (b) sintering the resulting material at a temperature of up to 250° C. to form an amorphous metal oxide coating on the surface of the substrate wherein:
 the metal oxide is selected from one or more of the group consisting of $Ag_2O$, $ZnO$, $ZrO_2$, $TiO_2$, $CuO$, and $Y_2O_3$;
 the metal oxide coating on the substrate surface is from 5 nm to 100 nm thick (e.g. from 5 nm to 50 nm thick, such as from 5 nm to 25 nm thick); and
 the root mean square roughness of the coating surface is from 0.1 to 0.7 nm.

It will be appreciated that any suitable variant of Pulsed Laser Deposition may be used herein. For example, when two or more materials are intended to be used in a gradiated fashion across a substrate, it may be convenient to make use of the Pulsed Laser Deposition Continuous Composition Spread Technique, which is a variant of Pulsed Laser Deposition. In addition, it will be appreciated that the resulting products of the above method are intended to cover the composite materials described hereinbefore.

As noted herein, the metal oxide coating layer is composed of amorphous metal oxides. As such, it is noted that the sintering step should be maintained at a suitable temperature—one that will not result in the crystallisation of the metal oxide(s) in the coating layer. With that in mind, the sintering step may be conducted at a temperature of up to 200° C., such as from 150 to 200° C. (e.g. 175° C.).

As will be appreciated, the composite materials disclosed herein may, in certain embodiments, be suitable for the growth of cells (e.g. in a culture or in an implant in need thereof). As such, there is provided a method of growing cells on a suitable composite material for the growth of cells as described herein, said method comprising the steps of:
 (a) providing a composite material as described herein and a first cell population;
 (b) applying the first cell population to the composite material; and
 (c) culturing the first cell population on the composite material to form a second cell population.

It will be appreciated that the above may be performed exclusively ex vivo. For example in a method of culturing cells. Suitable cells for cell culturing include, but are not limited to keratinocytes, fibroblasts, neural crest cells, neural stem cells, adipocytes, osteoblasts and bacterial cells (e.g. *salmonella* and *E. coli* cells). An advantage of the current coating materials for use in cell culturing and/or imaging is that there is generally no need to provide an extracellular and/or laminin coating, which would otherwise be required, though in some cases this may still be a requirement for some cell types—such as neural stem cells. This generally simplifies culturing and/or imaging procedures, which would otherwise require the additional step of coating the culturing surface with these materials.

As noted herein, the culturing vessel may comprise an optical slide that may then be imaged. As such, the method described hereinbefore may further comprise a step of imaging the cells following step (b) of the disclosed method of culturing.

The invention will now be further described with reference to the following non-limiting examples.

EXAMPLES

General Procedures
Imaging of Cells on the Coated Substrates

Figure 2:
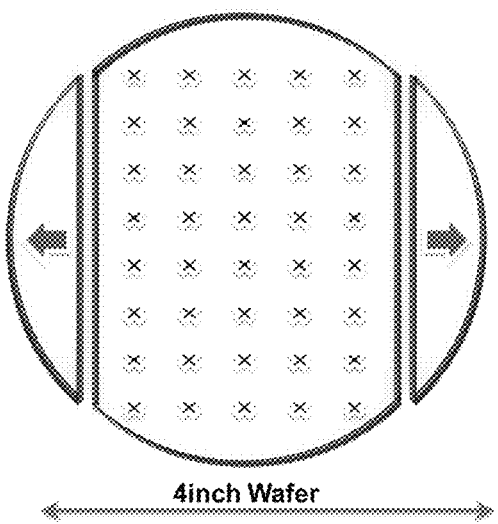
FIG. 2 Dimension and modification made to a coated substrate used for studying cellular properties on the oxide layers. The positions of the imaging frames are shown as "x"-marks.

The bright-field images of the cells on the substrates were acquired using a 10× objective on an Olympus IX83 Inverted Live Cell Microscope. Each image was taken at 1 cm intervals over the length and breadth (8 images by 5 images) of the substrate as shown in FIG. 2 ("x"-mark), yielding 40 images. These images were then stitched together using ImageJ.

Cell Cultures on the Coated Substrates

Different mammalian cell types were used. These include an immortalised human keratinocyte cell line (N/TERT-1s), primary human keratinocytes, primary human fibroblasts, a human neural stem cell line, human neural stem cells, human neural crest cells, a mouse pre-adipose cell line, a mouse schwannoma cell line, a dog MDCK epithelial cell line and human osteoblasts (MC3T3).

Culture of Keratinocytes—Primary human keratinocytes and a primary keratinocyte derived cell line, (N/TERT-1s) was used. Cells were thawed and cultured in keratinocyte serum-free medium supplemented with 0.2 ng/ml EGF and 25 µg/ml bovine pituitary extract, grown to 50% confluence at 37° C. and 5% $CO_2$, and sub-cultured using TrypLE Express (all purchased from Life Technologies, Singapore). For $Ca^{2+}$ varying experiments, keratinocyte serum-free medium without $Ca^{2+}$ was used and $Ca^{2+}$ was supplemented accordingly.

Culture of Fibroblasts—Cells were thawed and cultured in DMEM (Gibco, Singapore) supplemented with 10% FBS, grown to 50% confluence at 37° C. and 5% $CO_2$, and sub-cultured using TrypLE Express (all purchased from Life Technologies, Singapore). As with keratinocytes, for $Ca^{2+}$ varying experiments, DMEM (Gibco, Singapore) without $Ca^{2+}$ was used and $Ca^{2+}$ was supplemented accordingly. The mouse schwannoma cell line, dog MDCK epithelial cell line and the human osteoblasts (MC3T3) were grown under the same media condition as the adult human fibroblasts.

Culture of Neural Stem Cells—The ReNcell VM line (ReNVM) was created and distributed by ReNeuron Ltd (Donato, et al. 2007). It was derived from a ten-week old fetal midbrain tissue that was obtained from Kings College Hospital, London and is available through Millipore (cat # SCC008). Optimal results were achieved when cells were cultured in the NSC propagation medium described below. The media components are as follows: Neurobasal Medium (cat #21103-049-Gibco, Singapore) supplemented with L-Glutamine (1 mM) (Gibco, Singapore), KnockOut Serum Replacement (10%) (Gibco), B27 (2%) (Gibco), Wnt (40 ng/ml) (R&D Systems), cAMP (0.2 mM) (Sigma, Singapore), GDNF (20 ng/ml) (R&D Systems, Singapore), NGF (10 ng/ml) (R&D Systems, Singapore), BDNF (20 ng/ml) (R&D Systems, Singapore), Neurotrophin-3 (10 ng/ml) Sigma, Singapore), Heparin (10 Units/nil) (Sigma, Singapore) and L-Ascorbic acid (200 µM) (Sigma, Singapore).

Bacteria Culture—A single colony of wild type *Salmonella enterica* serovar *Typhimurium* strain 14028s was inoculated in 1.0 mL Luria-Bertani broth and grown overnight at 37° C. with shaking at 250 rpm. 2 µL of the overnight culture was inoculated in 198 µL of LB medium (without salt) containing 1% Tryptone and 0.5% Yeast Extract, in each well of the material library. The material was UV-sterilized before addition of the bacterial culture. Samples were then incubated under static conditions at 30° C. for two days to enable biofilm formation [S. K. Desai, R. S. Winardhi, S. Periasamy, M. M. Dykas, Y. Jie, L. J. Kenney, The horizontally-acquired response regulator SsrB drives a *Salmonella* lifestyle switch by relieving biofilm silencing, Elife 5 (2016)).

Example 1

A: Fabrication of $ZrO_2$—$Y_2O_3$ Coated Substrates

Thin film coatings of $ZrO_2$—$Y_2O_3$ on substrates were carried out using an adapted Pulsed Laser Deposition Continuous Composition Spread Technique (e.g. see *Review of Scientific Instruments* 72(6) (2001) 2673-2678). Round fused silica substrates of 4 inches in diameter were first cleaned by a series of washes (2 minutes each) in the following sequence:
1) trichloroethylene (J. T. Baker);
2) deionised water;
3) acetone (J. T. Baker);
4) deionised water;
5) methanol (J. T. Baker); and
6) deionised water.

Each step was followed by the removal of excess liquid by blowing under a steam of nitrogen.

The $ZrO_2$ target for Pulsed Laser Deposition (PLD) was prepared by compressing $ZrO_2$ powder (99.99% purity, Sigma Aldrich) into a pellet, which was then sintered at 1000° C. for 12 h. Similarly, $Y_2O_3$ powder (Alfa Aeser, 99.999% purity) was compressed into a pellet and sintered at 1000° C. for 12 hours. The $ZrO_2$—$Y_2O_3$ material thin films were prepared in an oxygen partial pressure of $3\times10^{-3}$ Torr (base vacuum pressure of $5\times10^{-7}$ Torr) at 200° C. The KrF excimer laser (248 nm) energy density was 2.15 J/cm² and the repetition rate was 5 Hz. The laser beam was focused at a 45° angle onto the target, with a target to sample distance of 84 mm. A series of 20 laser pulses onto the $Y_2O_3$ target and 24 laser pulses onto the $ZrO_2$ target were carried out repeatedly for 100 times.

Chemical Characterisation of the $ZrO_2$—$Y_2O_3$ Coated Substrate

Thickness was measured by Rutherford Backscattering Spectroscopy. Chemical distribution was measured through Particle Induced X-Ray Emission.

The surface composition of the substrate varied from around 95% of one material ($ZrO_2$ or $Y_2O_3$) on one side of the substrate, to about 50% in the middle, and then decreased to about 5% on the opposite side (FIGS. 1a and b). Such a chemical distribution of oxides can potentially be used to acquire a wide range of biological information.

The variation in the thickness was caused by the uneven deposition of the oxides as a majority of the material was deposited at the proximity of the plume, while less was deposited further away from the plume (i.e. a higher amount was deposited in line with the axis of the laser when positioned over each source). Though the thickness of the film (FIG. 1c) varied across the substrate, the variation was negligible as compared to the size of the cells (22 nm at distance of 5 cm—i.e. the thickness of the film on the substrate varies by 22 nm over a 5 cm line from the edge to the centre of the substrate). In addition, the surface roughness of the substrate which can affect cellular behaviour, was negligible as the variation was less than 1 nm (FIG. 1d).

B: Fabrication of ZnO—CuO and ZnO—$TiO_2$—$ZrO_2$ Coated Substrates

High purity powders of $Ag_2O$, ZnO, $ZrO_2$, $TiO_2$ (99.999% from Sigma) and CuO (99.995% from Alfa Aesar) were ground for several hours before each of the different powders was pressed into a pellet of 1 inch diameter, under a pressure of 200 MPa for 15 minutes. The pellets were then calcinated at 250° C. for 4 h, 1250° C. for 10 h, 1000° C. for 12 h, 1200° C. for 24 h and 900° C. for 48 h, respectively.

Quartz substrates of 4 inch diameter (from Plan Optik, thickness of 525 μm, Ra<0.5 nm, catalogue number: V015.04-0014) were first cleaned by series of washes (2 minutes each) in the following sequence:
1) trichloroethylene (J. T. Baker);
2) deionised water;
3) acetone (J. T. Baker);
4) deionised water;
5) methanol (J. T. Baker); and
6) deionised water.

Each step was followed by the removal of excess liquid by blowing under a steam of nitrogen.

The cleaned and dried substrates were coated with thin films via PLD under the following conditions:
1) substrate temperature of 200° C.;
2) base pressure of $5 \times 10^{-7}$ Torr, $O_2$ partial pressure of $3 \times 10^{-3}$ Torr;
3) target-substrate distance of 84 mm;
4) energy density of 2.1 $J/cm^2$ with laser frequency of 5 Hz; and
5) plume distance from the middle of the substrate of about 35 mm.

For the deposition of the binary material (ZnO—CuO), a series of 22 pulses onto the ZnO target and 29 pulses onto the CuO target were carried out repeatedly for 100 times. The substrate angular position was changed by 180 degrees for the deposition from each target.

For the deposition of the ternary material (ZnO—$TiO_2$—$ZrO_2$), a series of 20 pulses onto the ZnO target, 21 pulses onto the $TiO_2$ target and 24 pulses onto the $ZrO_2$ target were carried repeatedly for 100 times. The substrate angular position was changed by 120 degrees for the deposition from each target.

C: Modification of the Coated Substrates for Imaging Purposes

Various cell types were cultured on the $Y_2O_3$—$ZrO_2$ and the other substrates. To allow the coated substrates to fit onto the microscope stage for imaging purpose, a 2 cm segment was cut off from each side of the substrate (FIG. 2). The bottom region of FIG. 2 represents the maximal coating with $Y_2O_3$ and each cross represents a single frame that has been imaged across the substrate. A similar arrangement was used for the other substrates.

Example 2

Figure 3:
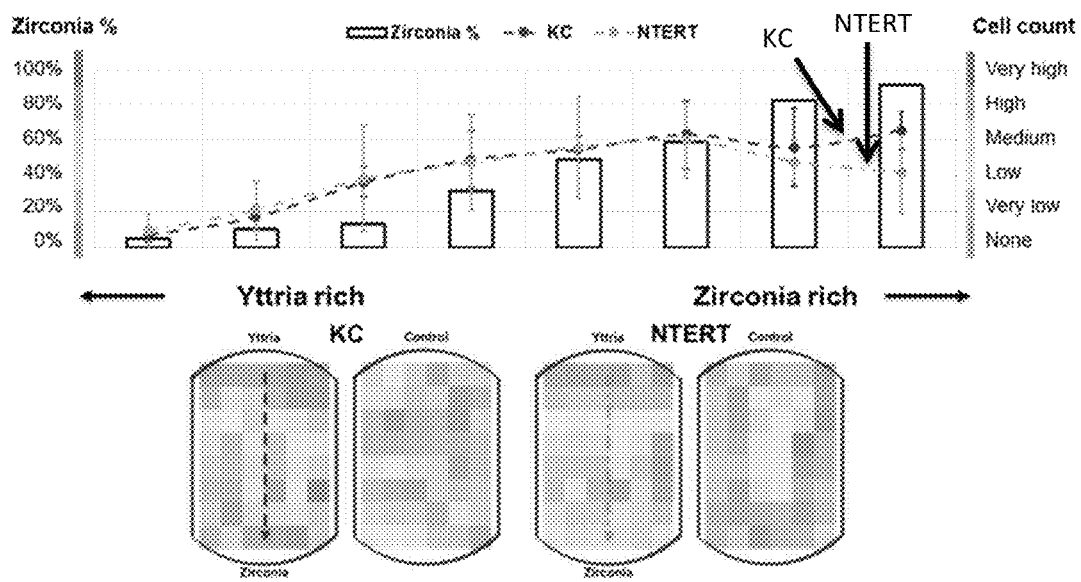
FIG. 3 Depicts the growth of keratinocytes (primary KC cells and immortalised NTERT cells) on a coated substrate having varying amounts of $Y_2O_3$ and $ZrO_2$: (a) depicts the average cell counts of KC and NTERT cells after 5 days of cell culture (n=2 for KC and n=3 for NTERT). Average values were obtained from the rows (total 8 rows in each of the 5 columns). The heat maps on the cartoon substrate represents the relative cell count at the various positions of the substrates (normalised to the highest cell concentration on a particular wafer sample); (b) provides representative images of KC grown on a coated substrate having varying amounts of $Y_2O_3$ and $ZrO_2$ (scale bar—20 μm); and (c) provides representative images showing cell distribution of KC at different 'zones' on the $Y_2O_3$—$ZrO_2$ coated substrate. The 'zones' represent different regions where cells exhibit distinct adhesion characteristics.
Figure 3:
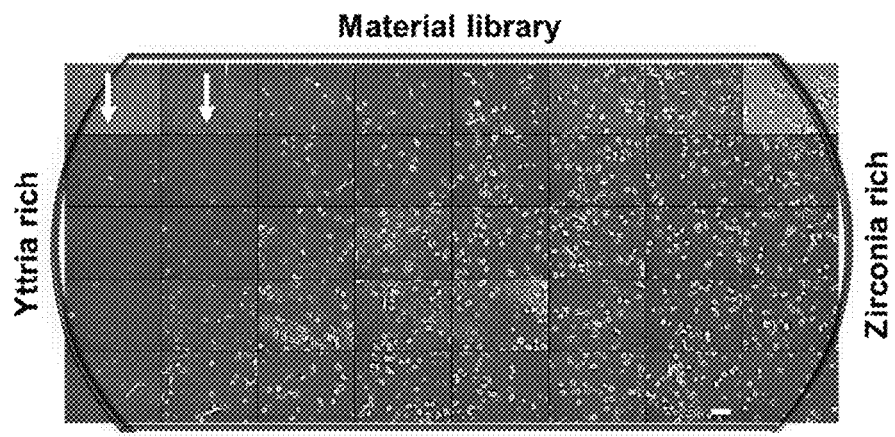
Figure 3:
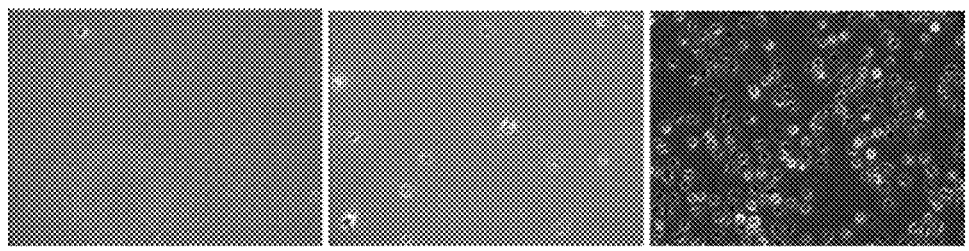

Growth of Immortalised Human Keratinocyte Cell Line (N/TERT-1s), Primary Human Keratinocytes (KC) on $Y_2O_3$—$ZrO_2$ Coated Substrates FIG. 3 shows the dependence of the keratinocytes cell count (average from the row) related to the chemical composition of the $Y_2O_3$—$ZrO_2$ coated substrate (cultured over 5 days). As shown in FIG. 3a, the cell counts for both cell lines increased with increasing $ZrO_2$ content on the surface. There were no significant differences between the primary KC cells and the NTERT cells, indicating that both cell lines have similar affinity to the oxide material surface.

For the control substrate ($SiO_2$ substrate without metal oxide coating), the cells grew everywhere with no specificity to any part of the substrate (not shown). However, for the $Y_2O_3$—$ZrO_2$ coated substrates, less cells were observed on the first two columns of the substrate ($Y_2O_3$>80%, indicated by the arrows) which suggests the preference of these cells towards $ZrO_2$ rich surface, and not $Y_2O_3$ rich surface (FIG. 3b). The images on FIG. 3b correlated well with the cell count data of FIG. 3a.

FIG. 3c depicts representative images of cell distribution at the different 'zones' on the $Y_2O_3$—$ZrO_2$ surface for keratinocytes (KC). The 'zones' represent different regions where cells exhibit distinct adhesion characteristics and the position of the 'zones' is unique for different cell types. At zone I, the inhibition zone (87%-95% $Y_2O_3$), no cells adhered onto the surface. However, it should be noted that, in comparison with fibroblasts (where the inhibition zone was ~65% to 90% $Y_2O_3$), this zone was relatively narrow for the KCs. At zone II, the transition zone (~80% $Y_2O_3$), more KCs adhered to the surface with a mix population of cells with healthy and unhealthy morphology. At zone III, the saturation zone (below 60% $Y_2O_3$), KCs with healthy morphology were observed on the surface.

Example 3

Figure 4:
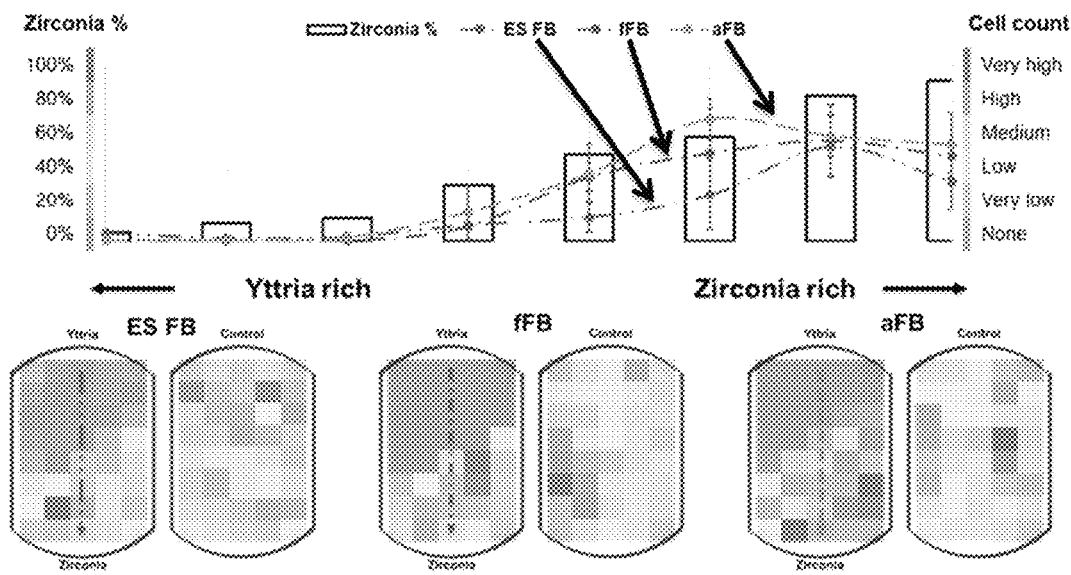
FIG. 4 Depicts the growth of primary human foreskin fibroblasts (fFB), adult fibroblasts (aFB) and fibroblast cell lines (ES-FB) on a coated substrate having varying amounts of $Y_2O_3$ and $ZrO_2$: (a) depicts the average cell counts of fFB, aFB and ES-FB cells after 5 days of cell culture (n=2). Average values were obtained from the rows (total 8 rows in each of the 5 columns). The heat maps on the cartoon substrate represent the relative cell count at the various positions of the substrates (normalised to the highest cell concentration on a particular wafer sample); (b) provides representative images of fFB grown on a coated substrate having varying amounts of $Y_2O_3$ and $ZrO_2$ after 5 days of cell culture (scale bar—20 μm). The arrow indicates half of the substrate where the cells start to adhere to the oxide surface (around 50% zirconia content); and (c) provides representative images showing cell distribution of human adult FBs at different 'zones' on the $Y_2O_3$—$ZrO_2$ coated substrate. The 'zones' represent different regions where cells exhibit distinct adhesion characteristics.
Figure 4:
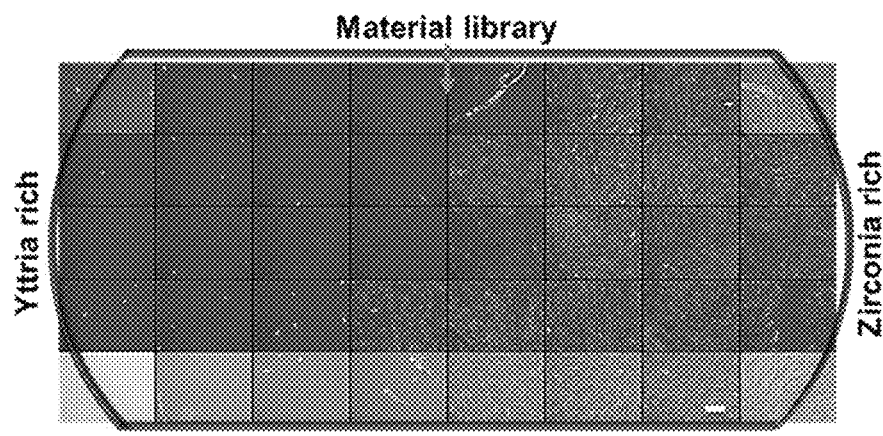
Figure 4:

Growth of Primary Human Foreskin Fibroblasts (fFB), Adult Fibroblasts (aFB) and Fibroblast Cell Lines (ES-FB) on $Y_2O_3$—$ZrO_2$ Coated Substrates FIG. 4 shows the adhesion of three fibroblasts cell lines, primary human foreskin (fFB) fibroblasts, adult fibroblast (aFB) and fibroblast cell line (ES-FB), cultured over 5 days on $Y_2O_3$—$ZrO_2$ coated substrates. For the control substrate ($SiO_2$ substrate without any metal oxide coating), the cells grew everywhere with no specificity to any part of the substrate (not shown). However, for the $Y_2O_3$—$ZrO_2$ coated substrate, minimal or no cell growth was observed for the first 4 columns of the metal oxide-coated substrate (where $Y_2O_3$>50%), while more cell growth was observed in regions with coating containing more than 50% $ZrO_2$ (FIG. 4a). This suggests that the fibroblast cell type has a different adhesion requirement to the previously shown keratinocytes. Interestingly, the highest number of cells was observed in the intermediate region (mostly in 2nd and 3rd row from the zirconia rich edge: 20%-40% $Y_2O_3$ doped surface) as shown in FIG. 4b. These fibroblast cells exhibit a very different adhesion pattern from the keratinocytes (in Example 1) and are less acceptable to the $Y_2O_3$ region.

Representative images in FIG. 4c show the cell distribution at the different 'zones' on the substrate for human adult fibroblasts (FBs). The 'zones' represent different regions where cells exhibit distinct adhesion characteristics; the position of the 'zones' is unique for different cell types. At zone I, the inhibition zone (65%-95% $Y_2O_3$), no cells adhered onto the surface. At zone II, the transition zone (~50% $Y_2O_3$), a small number of FBs adhered to the surface and at the saturation zone III (less than 45% $Y_2O_3$), a dense monolayer of FBs was observed on the surface.

Example 4

Growth of Human Neural Crest Cells (NCCs) on $Y_2O_3$—$ZrO_2$ Coated Substrates

Figure 5:
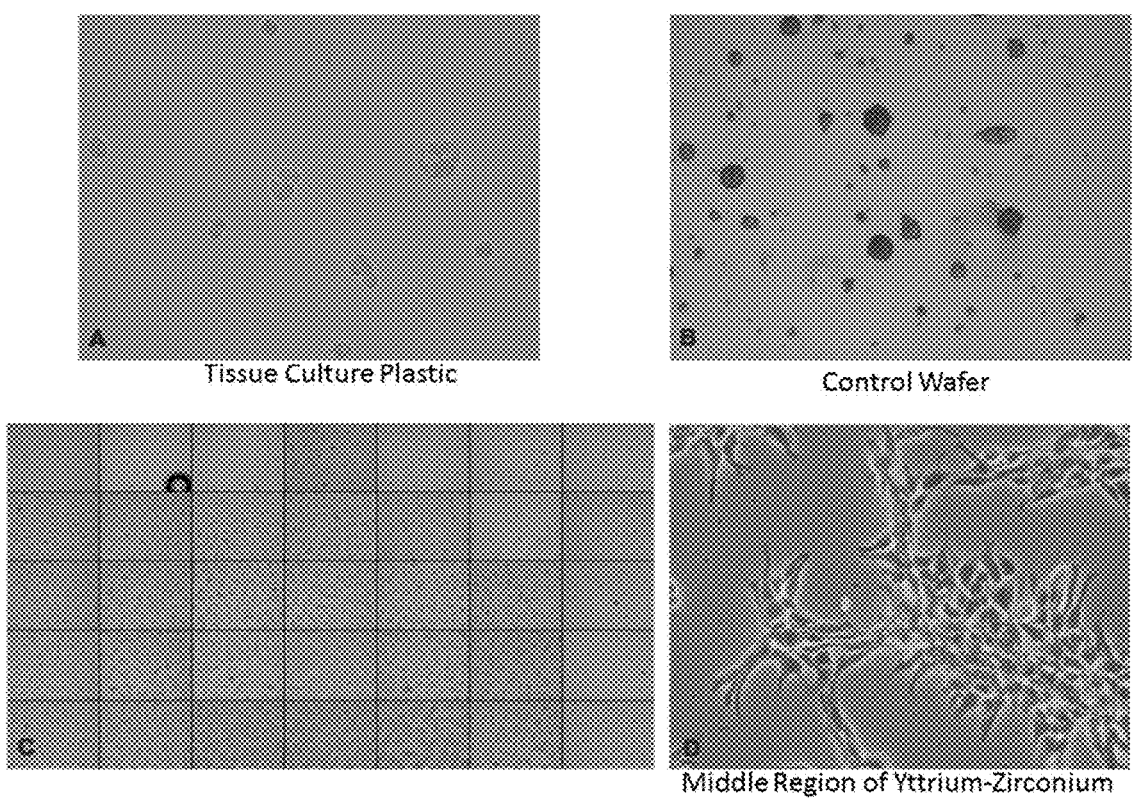
FIG. 5 Provides representative images of the growth of neural crest cells (NCCs), without extracellular matrix coating, on: (a) tissue culture plastic; (b) control $SiO_2$ substrate; and (c) $Y_2O_3$—$ZrO_2$ coated substrate, with (d) depicting a magnified middle region of the $Y_2O_3$—$ZrO_2$ coated substrate (approximate 1:1 of $Y_2O_3$—$ZrO_2$), showing the healthy and normal cell morphology of NCCs.

Unlike the previous cell types, which generally prefer to grow on $ZrO_2$ rich surface, human neural crest cells (NCCs) prefer to grow on the middle region which generally contains an equal mix of $Y_2O_3$ and $ZrO_2$. In addition, these cells adhered and proliferated without the need for an extracellular matrix coating (EMC). The NCCs generally require EMC to adhere onto tissue culture plastic or glass materials, so this is an unexpected result. FIG. 5a shows the morphology of NCCs on tissue culture surfaces (standard tissue culture dish) in the absence of EMC. These cells did not adhere with normal NCC morphology. A similar morphology was also observed for NCCs on uncoated $SiO_2$ substrates, in the absence of EMC (FIG. 5b).

However, for the substrate with $Y_2O_3$—$ZrO_2$ coating (without EMC), it was observed that the NCCs adhered to the middle region (FIG. 5c). When viewed at a higher magnification, the middle region of the coated substrate showed NCCs that adhered and proliferated normally, without any need for EMC (FIG. 5d). When the cells are differentiated, they tend to detach from the substrate indicating a change in their adhesion property upon differentiation.

Example 5

Growth of Neural Stem Cells (NSCs) on $Y_2O_3$—$ZrO_2$ Coated Substrates

Figure 6:
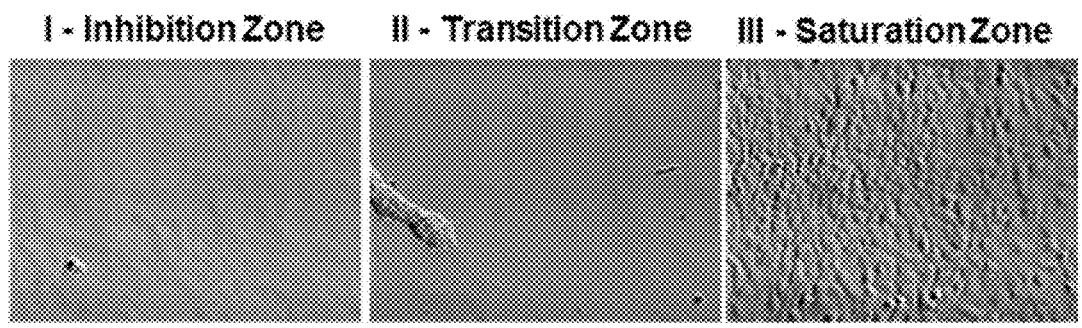
FIG. 6 Depicts the growth of neural stem cells (NSCs) on a coated substrate having varying amounts of $Y_2O_3$ and $ZrO_2$: (a) provides representative images showing cell distribution of NSCs at different 'zones' on a coated substrate having varying amounts of $Y_2O_3$ and $ZrO_2$ (with laminin coating); (b) Images of NSCs differentiating on a coated substrate having varying amounts of $Y_2O_3$ and $ZrO_2$ with laminin coating (scale bar—10 μm, n=3). Adhesion of the cells can be observed after 5 days of proliferation. After differentiation, the cells peeled off the $Y_2O_3$ coated surface.
Figure 6:
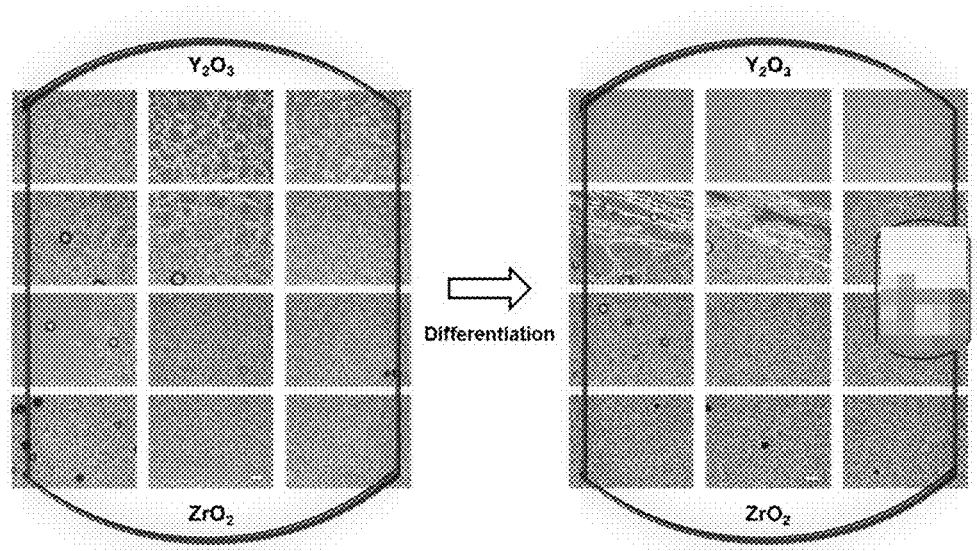

FIG. 6a shows the distribution of neural stem cells (NSCs) at the different 'zones' on the $Y_2O_3$—$ZrO_2$ coated substrate with laminin coating. At zone I, the inhibition zone (>90%-100% $Y_2O_3$), hardly any cells adhered onto the surface of the coated substrate. At zone II, the transition zone (~90% $Y_2O_3$), more NSCs adhered to the surface. However, the cells did not appear to be healthy as they showed round morphology and formed clumps. At zone III, the saturation zone (less than 80% $Y_2O_3$), a dense monolayer of NSCs was observed on the surface.

The NSCs adhered onto the $Y_2O_3$—$ZrO_2$ coated substrates with laminin coating after 5 days of proliferation (FIG. 6b). After differentiation, the cells peeled off the $Y_2O_3$ coated surface. On the other hand, the cells were not able to adhere to the control substrate ($SiO_2$ substrate) even after it was coated with laminin. In addition, NSCs showed some distinction in adhesion pattern based on the amount of $Y_2O_3$ present. Also, upon differentiation to neurons, the adhesion pattern changed as shown in FIG. 6b, which became similar to that of fibroblasts.

Example 6

Growth of Adipocytes on $Y_2O_3$—$ZrO_2$ Coated Substrates

Figure 7:
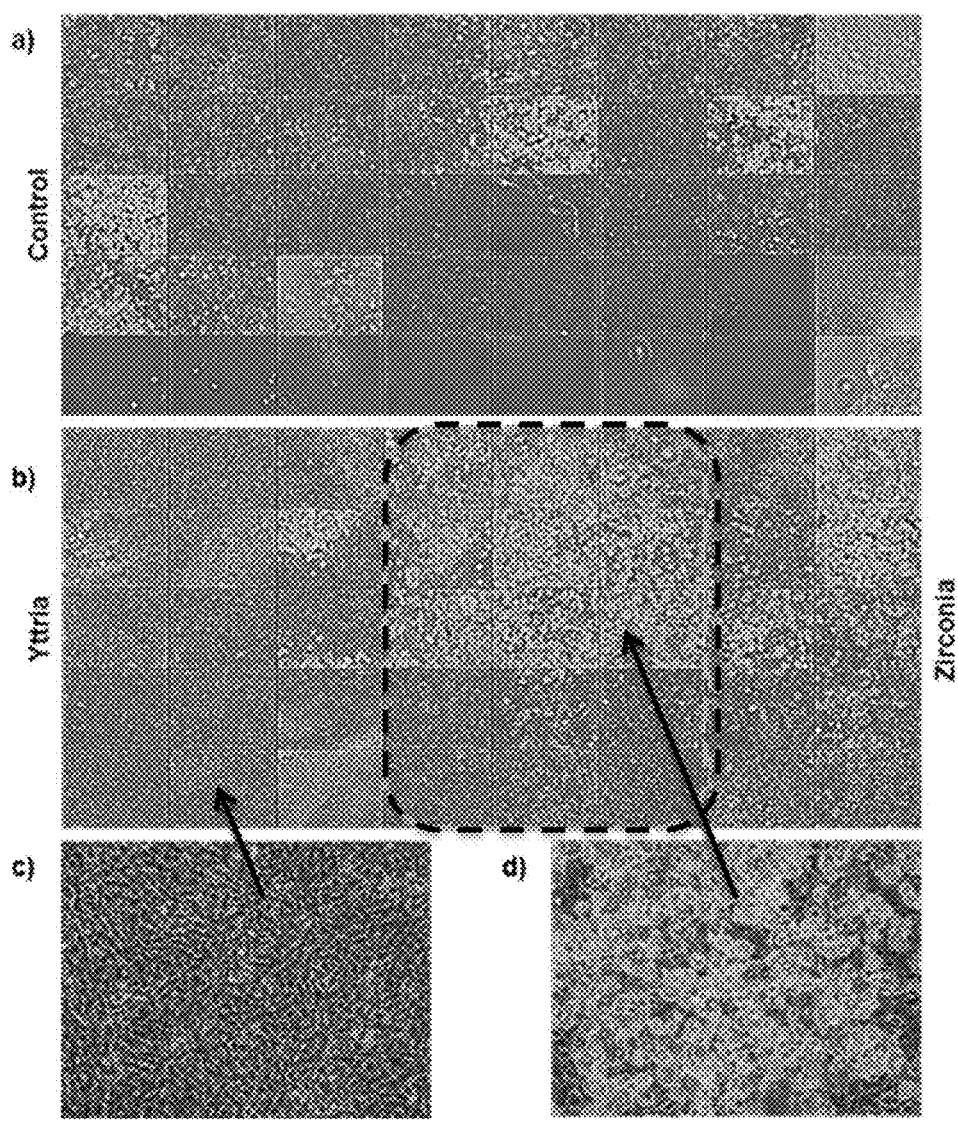
FIG. 7 Depicts lipid droplet formation by adipocytes grown on: (a) a control substrate; (b) a $Y_2O_3$—$ZrO_2$ coated substrate; (c) immature cells with no formation of lipid droplets; and (d) mature cells with lipid droplets formed. An increase in the differentiated adipocytes with lipid formation was observed on the (b) $Y_2O_3$—$ZrO_2$ coated substrates as opposed to (a) the control substrate.

Pre-adipocytes have the potential to differentiate to form adipocytes or fat cells which when mature, contain a lipid droplet surrounding the cytoplasm. Mouse pre-adipocytes were seeded onto a $Y_2O_3$—$ZrO_2$ coated substrate and a control substrate ($SiO_2$; no metal oxide coating). A higher degree of cell proliferation was observed on the metal oxide-coated substrate as compared to the control substrate. When both substrates were confluent, the cells were incubated with differentiation media to induce differentiation. After differentiation, the cells on the metal oxide-coated substrate showed an increase in the formation of lipids as opposed to the cells on the control substrate (FIG. 7).

To validate the above observation, fluorescence imaging of the adipocytes stained with GFP-BODIPY (green fluorescent protein-tagged boron-dipyrromethene which stains lipid droplets), and RFP-PPARA (red fluorescent protein-tagged ligand for peroxisome proliferators-activated receptor A which targets the PPARA expressed on mature adipocytes) was carried out.

Figure 8:
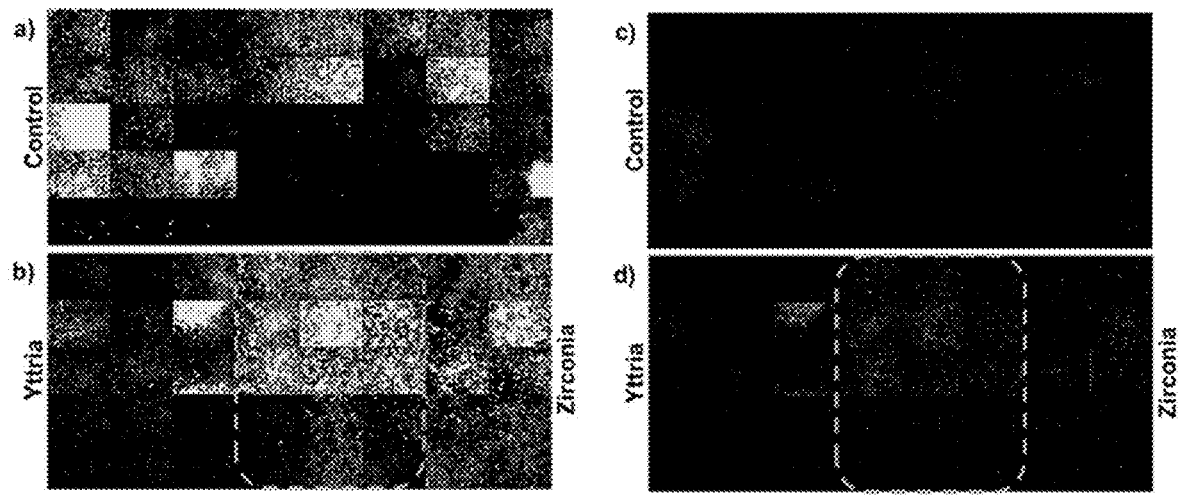
FIG. 8 Depicts fluorescent staining of adipocytes. GFP-BODIPY staining of lipid droplets on cells grown on a: (a) control substrate (no metal oxide coating); and (b) $Y_2O_3$—$ZrO_2$ coated substrates. RFP-PPARA staining of cells grown on a (c) control substrate (no metal oxide coating), and on a (d) $Y_2O_3$—$ZrO_2$ coated substrate.

Higher fluorescence intensities due to the staining of lipid droplets (FIGS. 8a and b) and PPARλ (FIGS. 8c and d) were observed on the adipocytes grown on $Y_2O_3$—$ZrO_2$ coated substrates as compared to those in the control setup. As observed in FIG. 8, higher concentrations of lipid droplets and mature adipocytes were localised at the central region (containing a mix of $Y_2O_3$ and $ZrO_2$) of the metal oxide-coated substrate.

Other Mammalian Cells

Other mammalian cells, such as dog MDCKs and mouse schwannoma cells (RT4-D6-P2T from ATCC) were also tested. Results indicate that while the schwannoma cells strongly preferred the $ZrO_2$ region, while the MDCK cells were dispersed throughout the material library, with fewer cells at the region with the highest $Y_2O_3$ concentration.

Example 7

Figure 9:
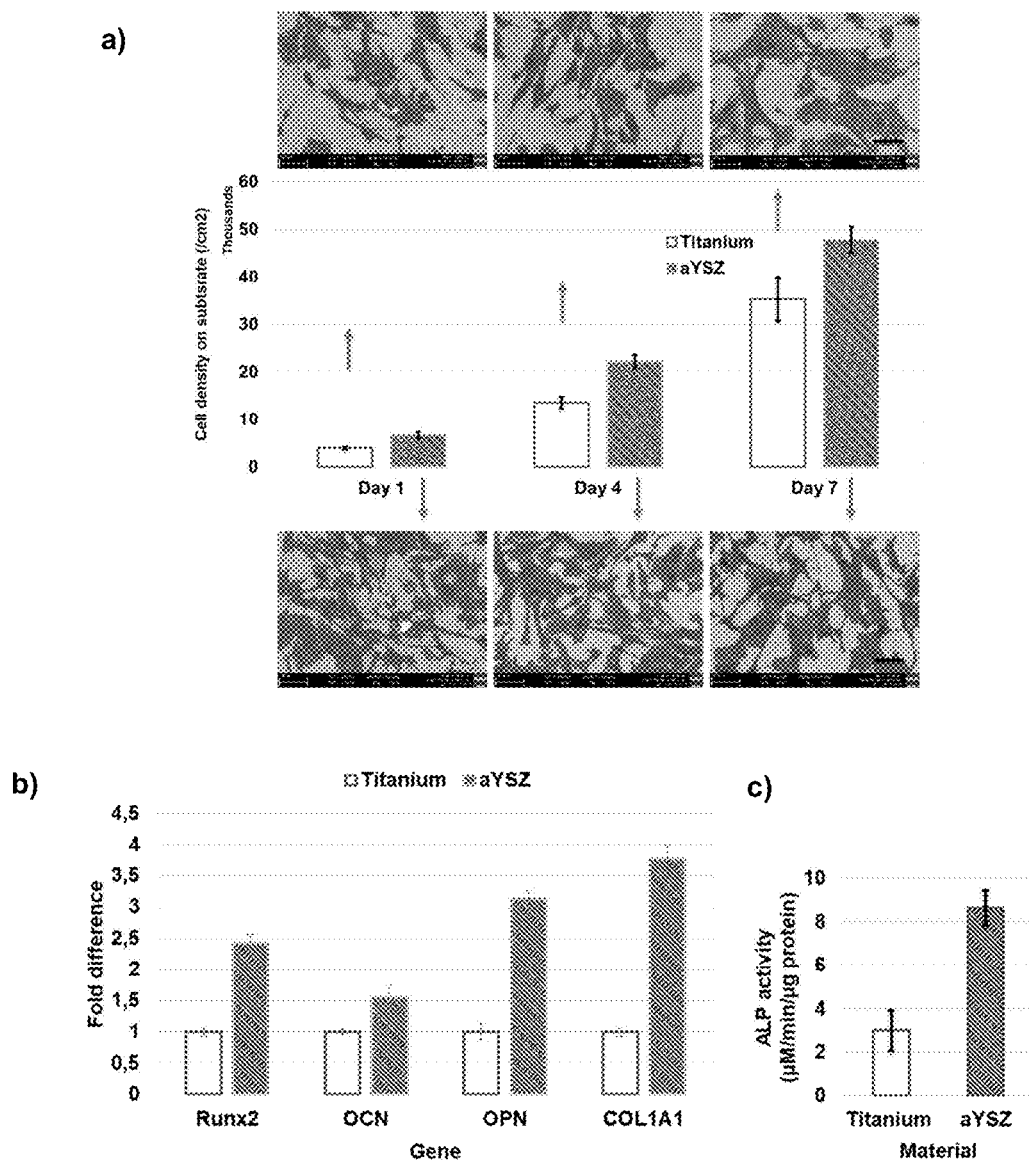
FIG. 9 Depicts: (a) proliferation of human osteoblasts on a titanium and an amorphous yttria-stabilised-zirconia (aYSZ; 95 wt % $ZrO_2$ and 5 wt % $Y_2O_3$) coated titanium substrate (n=3, scale bars—100 μm); comparison of (b) various gene expressions; and (c) alkaline phosphatase activity of the osteoblasts grown separately on a titanium and a yttria-stabilised-zirconia coated titanium substrate.

Growth of Osteoblast Cells on Yttria-Stabilised-Zirconia Coated Titanium or Glass Substrates Titanium (Ti) is a common material for bone implants. When human osteoblast cells were grown separately on a Ti substrate and on a Ti substrate coated with $ZrO_2$ doped with 5% of $Y_2O_3$ using the method described hereinbefore, a significant increase in cell numbers was noted on the metal oxide-coated Ti substrate as compared to the non-coated Ti substrate, over a period of 1, 4 and 7 days (FIG. 9a).

Other than the higher osteoblast cell counts, further studies also revealed an increase in COL1A1 expression and other bone-related gene expressions (FIGS. 9b and c), together with $Ca^{2+}$ deposition in cells grown on the metal oxide-coated Ti substrates. These results are indicative of bone formation.

Figure 10:
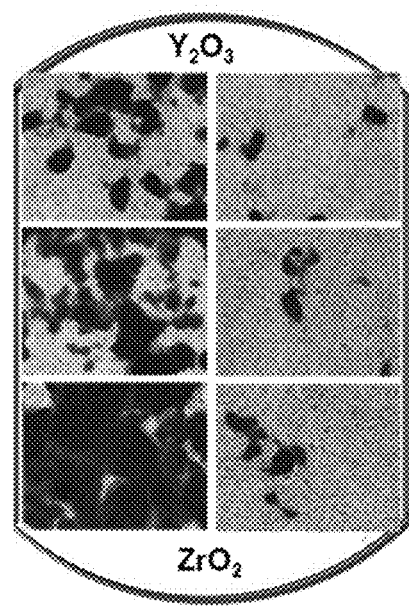
FIG. 10 Provides representative images of mouse osteoblasts precursor MC3T3 grown on $Y_2O_3$—$ZrO_2$ coated glass and non-coated glass substrates, stained with Alizarin Red.

Mouse osteoblasts precursor MC3T3 were grown on a $Y_2O_3$—$ZrO_2$ coated glass substrate and uncoated glass substrate. The differentiated cells (21 days old) were stained with Alizarin Red to detect calcium (Ca) deposition. A higher deposition of Ca was observed in the cells grown on the metal oxide-coated surface as compared to the glass control (FIG. 10). The $ZrO_2$ rich regions of the substrate showed a stronger staining than the $Y_2O_3$ rich regions.

The above suggests that the choice of substrate material (whether it is Ti or glass substrates) for the metal oxide-coated surface did not have significant effects on the cell responses, such as cell adhesion, proliferation, differentiation and deposition of Ca. As most implant materials or coatings that require cellular interaction involve an elevated expression of osseointegration, this therefore holds promise for the modification of implants using selected oxides so as to control the selectivity and specificity of cell growth over them.

Example 8

Bacterial Growth on Binary/Ternary Metal Oxide-Coated Substrates

Figure 11:
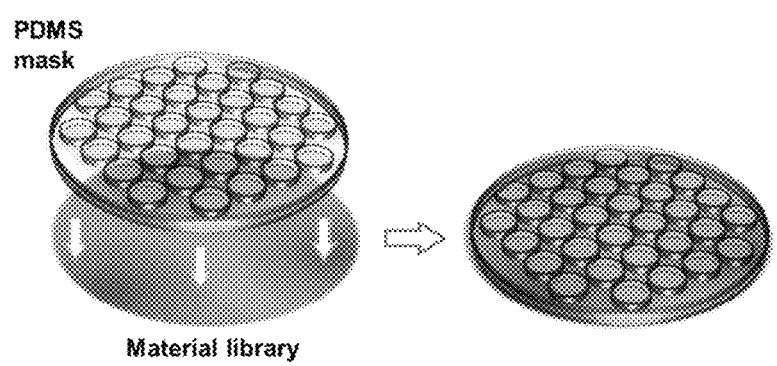
FIG. 11 Depicts the placement of PDMS mask over the metal oxide-coated substrate to divide the substrate into 32 circular compartments, prior to culturing the bacteria on it.

The metal oxide-coated circular substrate was divided into 32 circular compartments using a custom-made polydimethylsiloxane (PDMS) mask (FIG. 11). *Salmonella enterica* was cultured for 48 hours in static conditions and stained with crystal violet to determine the amount of deposited biofilm.

Figure 12:
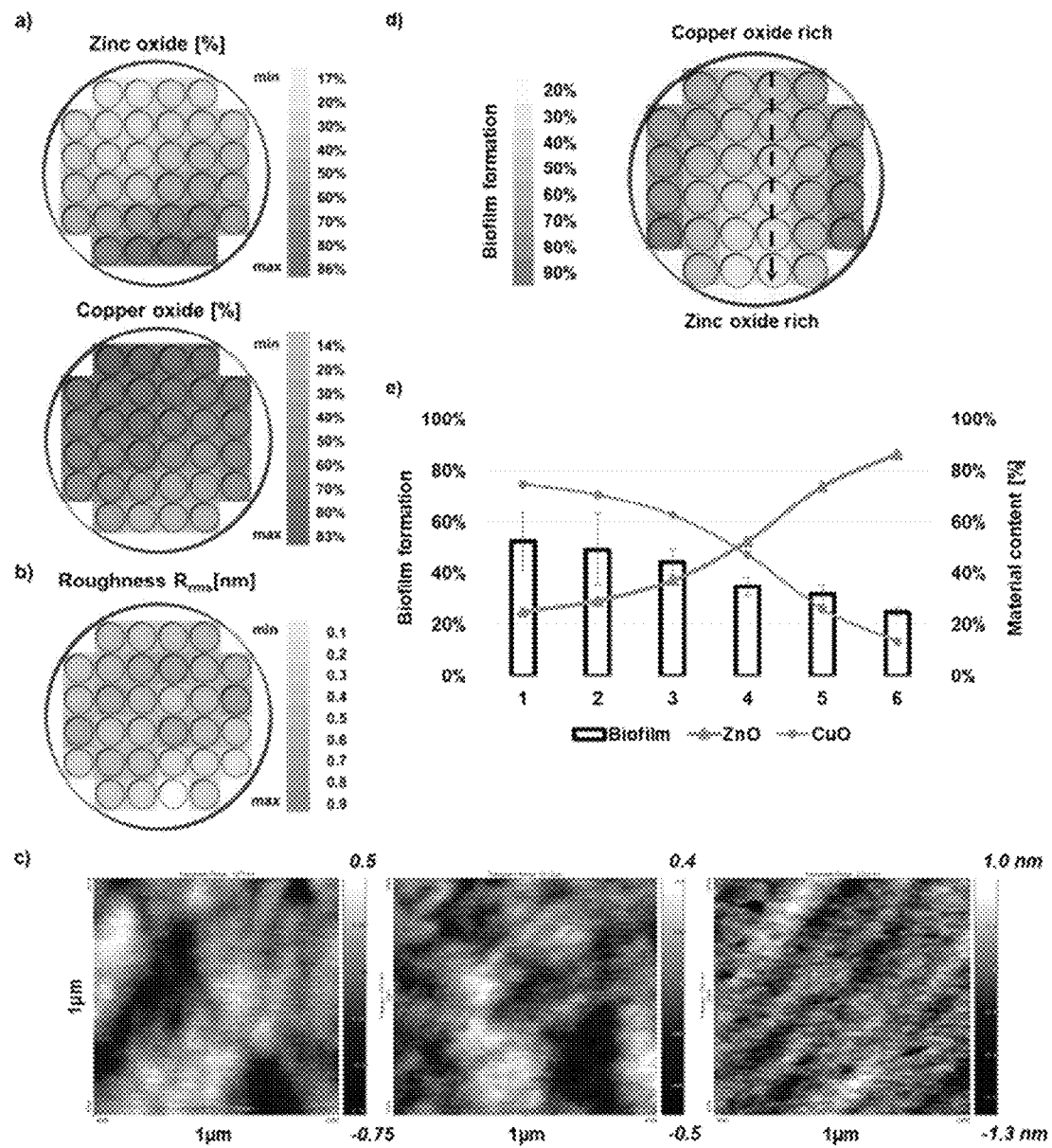
FIG. 12 Depicts surface characterisation and biofilm formation on the binary metal oxide-coated substrate: (a) composition of ZnO and CuO across the substrate surface; (b) roughness (0.4 nm average) of the surface; (c) AFM images of sample surfaces; (d) biofilm formation results (normalised to control) across the substrate; (e) a plot of the biofilm formation and the material content at the 6 positions on the substrate as indicated by the arrow in (d) (n=3).

Zinc oxide (ZnO) and copper (II) oxide (CuO) were used for the binary metal oxide-coated substrate. Variation in the metal oxides composition across the substrate did not have a correlation to the roughness of the surface. In this case, the roughness was relatively low throughout the sample, with an average rms roughness of 0.4 nm (FIG. 12b). The AFM (atomic force microscopy) images of the sample surfaces were as shown in FIG. 12c.

It was observed that the composition of the substrate surface had an effect on biofilm formation (FIG. 12d). Both metal oxides retarded biofilm formation as compared to the control quartz sample. A clear, almost linear relationship between the variation in the amount of the metal oxides and the amount of biofilm formed can be observed in FIG. 12e. The results at sample boundaries (top and bottom) generally reached the values achieved on pure (100%) oxide surfaces.

Zinc oxide (ZnO), zirconium oxide ($ZrO_2$) and titanium oxide ($TiO_2$) were used for the ternary metal oxide-coated substrate. FIG. 13a shows the distribution of various metal oxides across the substrate. FIGS. 13b and c show the roughness of the substrate surface and the AFM images of the surface respectively. The amount of biofilm formed on a ternary library did not correlate linearly with the metal oxide composition gradient like in the binary system (FIG. 12e). In this case, two distinct trends can be observed as shown in FIG. 13d.

The first trend as shown in FIG. 13e (following the arrow on the right in FIG. 13d) was similar to the one obtained for the binary material. It showed that an increase in ZnO content (with a decrease in $ZrO_2$ content) resulted in higher amount of biofilm formed.

The other trend as shown in FIG. 13f, following the left arrow in FIG. 13d, suggests that both ZnO and $TiO_2$, when present in a substantial amount (>90%), reduced the formation of biofilm.

Figure 13:
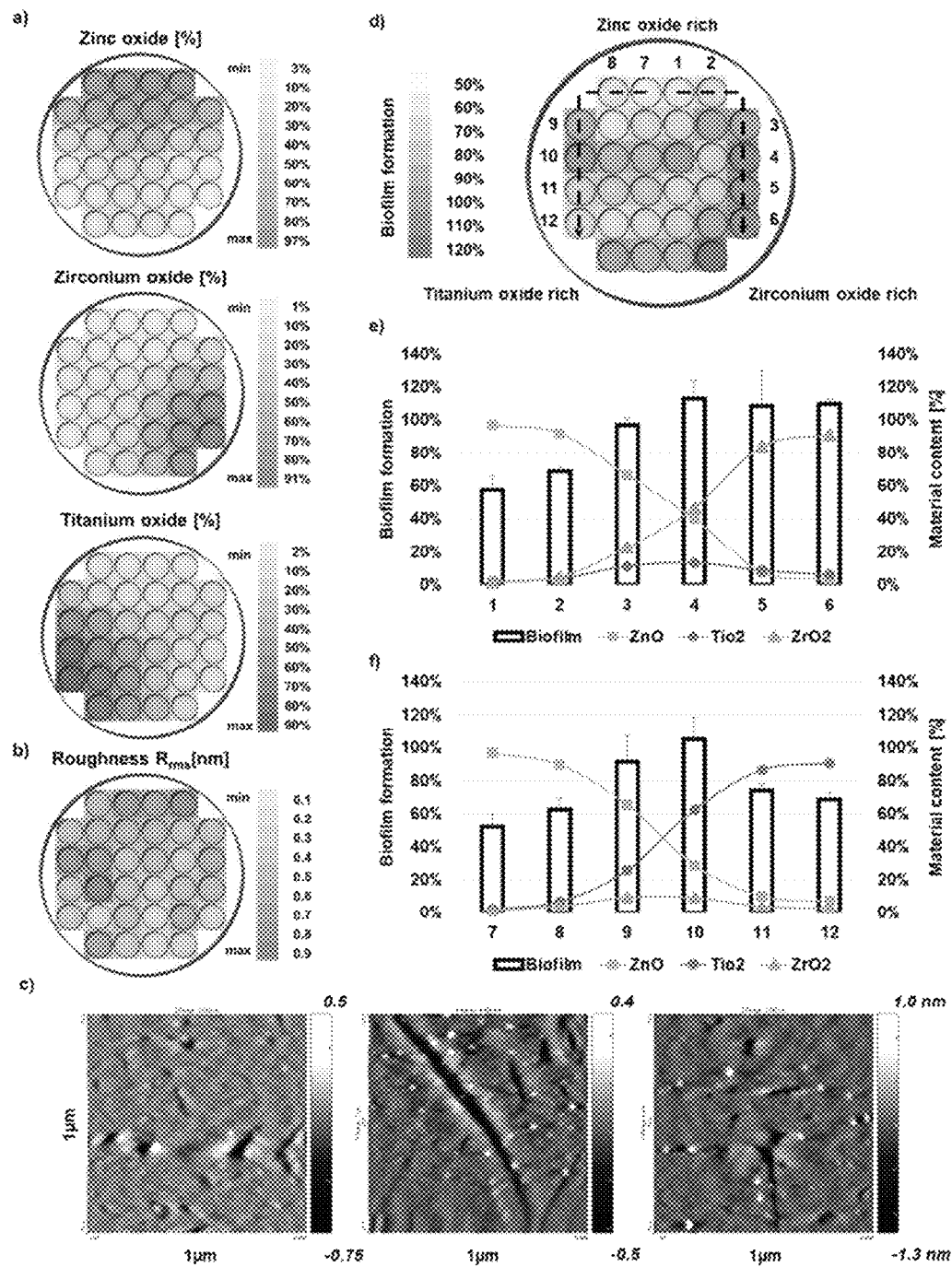
FIG. 13 Depicts surface characterisation and biofilm formation on the ternary metal oxide-coated substrate: (a) composition of ZnO, $ZrO_2$ and $TiO_2$ across the substrate surface; (b) roughness (0.52 nm average) of the surface; (c) AFM images of sample surfaces; (d) biofilm formation results (normalised to control) across the substrate; (e) a plot of the biofilm formation and the material content at well 1-6 of the substrate, as indicated by the right arrow in (d) (n=3); (f) a plot of the biofilm formation and the material content at well 7-12 of the substrate, as indicated by the left arrow in (d) (n=3).

However, as shown in FIG. 13, the anti-biofilm nature of the metal oxide coatings is not the direct product of any one of the oxides, but is rather the result of the combination of all three metal oxides in a non-linear fashion.

Example 9

Figure 14:
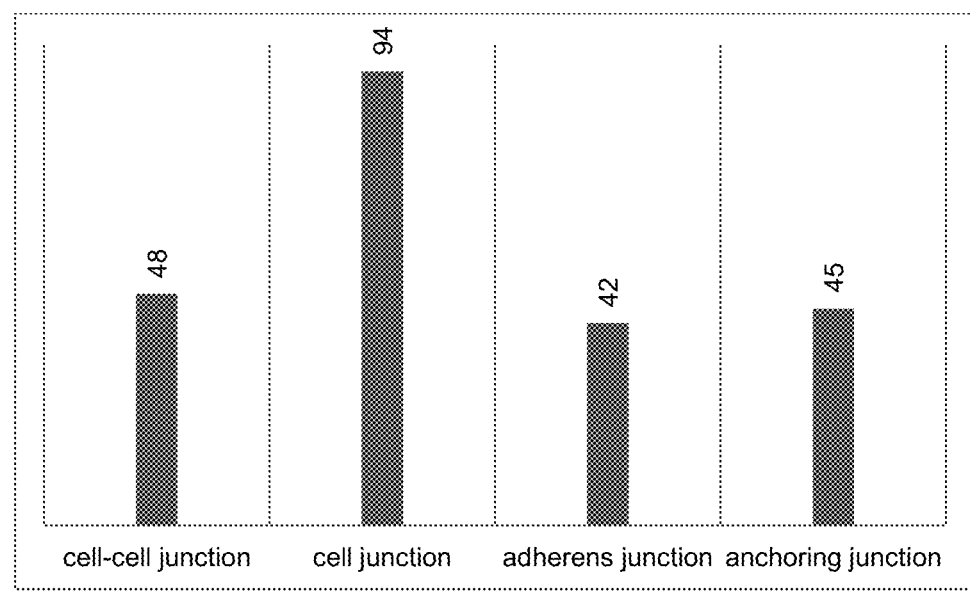
FIG. 14 Depicts the number of significantly up regulated adhesion related genes observed when cells grown on $ZrO_2$ for 12 hours were compared to cells grown on $Y_2O_3$ for 12 hours.

Comparison of Gene Expression Between Cells Grown on $Y_2O_3$-Coated and $ZrO_2$-Coated Substrates To understand the adhesion mechanism involved in mitigating cell-substrate adhesion, the gene regulations of adult human fibroblasts cells seeded on $Y_2O_3$-coated and $ZrO_2$-coated substrates were studied. RNA from the cells were extracted after they were seeded and grown for 12 h on the $Y_2O_3$ and $ZrO_2$ thin film coated substrates. This was carried out in three biological replicates and was followed by sequencing of the RNA samples. FIG. 14 shows the number of genes that were significantly up-regulated in cells grown on $ZrO_2$ as compared to cells grown on $Y_2O_3$. From the results, different adhesion related genes, which fall into the categories of cell-cell junction, cell junction, adherens junction and anchoring junction were significantly up-regulated, with 18 genes being common among all of them.

The invention claimed is:

1. A composite material comprising:
a substrate having a surface; and
an amorphous metal oxide coating on the surface of said substrate, where the amorphous metal oxide coating comprises an amorphous contact surface of the composite material, wherein:
the amorphous metal oxide coating comprises a blend of $ZrO_2$ and $Y_2O_3$, wherein the blend of $ZrO_2$ and $Y_2O_3$ comprises individual $ZrO_2$ entities and individual $Y_2O_3$ entities; and
the amorphous metal oxide coating on the surface of the substrate is from 5 nm to 100 nm thick.

2. The composite material according to claim 1, wherein the amorphous metal oxide coating further comprises one or more of $Ag_2O$, ZnO, $TiO_2$, and CuO.

3. The composite material according to claim 1, wherein a wt % content of each metal oxide varies throughout the amorphous metal oxide coating, such that at any given location one of the metal oxides is present in an amount of from 0 wt % to 100 wt %.

4. The composite material according to claim 3, wherein a wt % content of each metal oxide varies throughout the amorphous metal oxide coating, such that at any given location one of the metal oxides is present in an amount of from 5 wt % to 95 wt %.

5. The composite material according to claim 1, wherein a wt % content of each metal oxide is constant throughout the amorphous metal oxide coating, such that each metal oxide is present in an amount of from 0.1 wt % to 99.5 wt %.

6. The composite material according to claim 5, wherein $ZrO_2$ is present in an amount of from 1 wt % to 99 wt % throughout the amorphous metal oxide coating, with a balance being $Y_2O_3$.

7. The composite material according to claim 6, wherein $ZrO_2$ is present in an amount of from 15 wt % to 85 wt % throughout the amorphous metal oxide coating, with a balance being $Y_2O_3$.

8. The composite material according to claim 7, wherein $ZrO_2$ is present in an amount of from 20 wt % to 80 wt % throughout the amorphous metal oxide coating, with a balance being $Y_2O_3$.

9. The composite material according to claim 8, wherein $ZrO_2$ is present in an amount of from 50 wt % throughout the amorphous metal oxide coating, with a balance being $Y_2O_3$.

10. The composite material according to claim 1, wherein the substrate is selected from the group consisting of titanium and silicon oxide.

11. The composite material according to claim 1, wherein the substrate is in a form of a transparent slide suitable for microscopy or in the form of a medical implant.

12. The composite material according to claim 11, wherein:
(a) the substrate is a temporary medical implant where the amorphous metal oxide coating comprises from 65 to 99.5 wt % of $Y_2O_3$;
(b) the substrate is a permanent medical implant where the amorphous metal oxide coating comprises from 50 to 99.5 wt % of $ZrO_2$; or
(c) the substrate is an intraocular lens where the amorphous metal oxide coating comprises from 65 to 99.5 wt % of $Y_2O_3$.

13. The composite material according to claim 1, wherein the amorphous metal oxide coating has a root mean square roughness of from 0.1 to 0.7 nm.

* * * * *